(12) United States Patent
Iannitti et al.

(10) Patent No.: US 11,375,889 B2
(45) Date of Patent: Jul. 5, 2022

(54) DEVICES, SYSTEMS, AND METHODS FOR IMAGE GUIDED LAPAROSCOPIC SURGERY

(71) Applicant: THE CHARLOTTE-MECKLENBURG HOSPITAL AUTHORITY, Charlotte, NC (US)

(72) Inventors: David A. Iannitti, Charlotte, NC (US); John B. Martinie, Charlotte, NC (US)

(73) Assignee: THE CHARLOTTE-MECKLENBURG HOSPITAL AUTHORITY, Charlotte, NC (US)

(*) Notice: Subject to any disclaimer, the term of this patent is extended or adjusted under 35 U.S.C. 154(b) by 54 days.

(21) Appl. No.: 15/849,852

(22) Filed: Dec. 21, 2017

(65) Prior Publication Data

US 2018/0177390 A1    Jun. 28, 2018

Related U.S. Application Data

(60) Provisional application No. 62/439,287, filed on Dec. 27, 2016.

(51) Int. Cl.
*A61B 1/313* (2006.01)
*A61B 34/20* (2016.01)
(Continued)

(52) U.S. Cl.
CPC ........ *A61B 1/3132* (2013.01); *A61B 1/00045* (2013.01); *A61B 18/1445* (2013.01); *A61B 34/20* (2016.02); *A61B 34/25* (2016.02); *A61B 17/00234* (2013.01); *A61B 17/07207* (2013.01); *A61B 17/29* (2013.01); *A61B 90/361* (2016.02); *A61B 2017/00017* (2013.01); *A61B 2017/3413* (2013.01); *A61B 2018/0063* (2013.01);
(Continued)

(58) Field of Classification Search
CPC .............. A61B 1/3132; A61B 18/1445; A61B 2034/2051; A61B 2018/0063; A61B 2018/00607; A61B 17/00234; A61B 17/29; A61B 34/20
See application file for complete search history.

(56) References Cited

U.S. PATENT DOCUMENTS 7,728,868 B2   6/2010   Razzaque et al.
8,340,379 B2   12/2012  Razzaque et al.
(Continued)

OTHER PUBLICATIONS

U.S. Appl. No. 62/413,925, filed Oct. 27, 2016.

*Primary Examiner* — Sarah A Simpson
(74) *Attorney, Agent, or Firm* — J. Clinton Wimbish; Nexsen Pruet, PLLC (57) ABSTRACT

In one aspect, devices for image guided laparoscopic surgery are disclosed. Such devices can comprise a shaft, a surgical component, a handle, and one or more sensors. The shaft comprises a proximal end and a terminal end that opposes the proximal end. The surgical component is disposed at the terminal end of the shaft, and the handle extends from the proximal end of the shaft. The handle comprises one or more actuating components configured to actuate the surgical component. The one or more sensors are disposed on or over the handle, and are configured to detect and/or track movement of the handle and/or actuation of one or more of the actuating components.

14 Claims, 3 Drawing Sheets

(51) Int. Cl.
  *A61B 1/00* (2006.01)
  *A61B 34/00* (2016.01)
  *A61B 18/14* (2006.01)
  *A61B 17/00* (2006.01)
  *A61B 90/00* (2016.01)
  *A61B 18/00* (2006.01)
  *A61B 17/072* (2006.01)
  *A61B 17/29* (2006.01)
  *A61B 17/34* (2006.01)

(52) U.S. Cl.
  CPC ........... *A61B 2018/00601* (2013.01); *A61B 2018/00607* (2013.01); *A61B 2018/00982* (2013.01); *A61B 2034/2051* (2016.02); *A61B 2034/2055* (2016.02); *A61B 2034/2063* (2016.02); *A61B 2090/0811* (2016.02); *A61B 2090/378* (2016.02)

(56) References Cited

U.S. PATENT DOCUMENTS

| | | |
|---|---|---|
| 8,350,902 B2 | 1/2013 | Razzaque et al. |
| 8,482,606 B2 | 7/2013 | Razzaque et al. |
| 8,554,307 B2 | 10/2013 | Razzaque et al. |
| 8,585,598 B2 | 11/2013 | Razzaque et al. |
| 8,641,621 B2 | 2/2014 | Razzaque et al. |
| 8,670,816 B2 | 3/2014 | Green et al. |
| 8,690,776 B2 | 4/2014 | Razzaque et al. |
| 8,831,310 B2 | 9/2014 | Razzaque et al. |
| 9,107,698 B2 | 8/2015 | Razzaque et al. |
| 9,282,947 B2 | 3/2016 | Razzaque et al. |
| 9,364,294 B2 | 6/2016 | Razzaque et al. |
| 9,398,936 B2 | 7/2016 | Razzaque et al. |
| 9,675,319 B1 | 6/2017 | Razzaque et al. |
| 2010/0305439 A1* | 12/2010 | Shai ............... A61B 18/02 600/439 |
| 2013/0218007 A1* | 8/2013 | Petteys ............ A61B 17/808 600/424 |
| 2014/0031674 A1* | 1/2014 | Newman ........... A61B 8/0841 600/424 |
| 2014/0246474 A1* | 9/2014 | Hall ............ A61B 17/07207 227/175.1 |
| 2014/0343416 A1* | 11/2014 | Panescu ............ A61B 34/30 600/431 |
| 2015/0083781 A1* | 3/2015 | Giordano .......... A61B 17/068 227/176.1 |
| 2015/0305797 A1* | 10/2015 | Hassoun ............. A61B 17/29 606/27 |
| 2017/0202611 A1* | 7/2017 | Shin ................... A61N 1/06 |

* cited by examiner

DEVICES, SYSTEMS, AND METHODS FOR IMAGE GUIDED LAPAROSCOPIC SURGERY

CROSS REFERENCE TO RELATED APPLICATIONS

This application claims priority pursuant to 35 U.S.C. § 119(e) to U.S. Provisional Patent Application Ser. No. 62/439,287, filed on Dec. 27, 2016, which is hereby incorporated by reference in its entirety.

FIELD

The subject matter herein relates generally to laparoscopic surgery and, more particularly, to devices, systems, and methods for image guided laparoscopic surgery.

BACKGROUND

Minimally invasive surgery, such as laparoscopy, offers many advantages compared to traditional open surgery techniques. For example, as patients may experience less pain, shorter hospital stays, and reduced recovery times. For these reasons and others, the demand for minimally invasive surgery is growing.

Performing laparoscopy on solid organs (e.g., the liver, kidney, etc.), or portions thereof is difficult, in part due to the difficulty of visualizing and mapping vital structures both prior to and during surgery on a solid organ. The inherent loss of the surgeon's tactile sensation during laparoscopy especially contributes to difficulty in navigating medical devices to and/or around targeted tissue during surgery, as compared to traditional open surgery techniques. Further, solid organs are not stationary or fixed within the body. Rather, the organs move in response to being probed or manipulated during surgery. These movements further complicate the surgeon's ability to navigate medical devices to and/or around vital structures.

Current methods of performing, laparoscopic surgery on a solid organ include blindly dividing the organ along an arbitrary organ transection line with a dividing device (e.g., shears, energy devices, etc.). Any vital structures that are encountered during dissection of the tissue are formally ligated using a stapling or clipping device. Blind dissection of the organ is problematic, however, as it can lead to unnecessary bleeding and/or injury to vital structures that are encountered during dissection.

Therefore, a need exists for improved devices, systems, and methods of image guided laparoscopic surgery, particularly for identifying vital structures before dissection of a solid organ and for more accurately navigating medical devices to and/or around the vital structures during dissection. The devices, systems, and methods described herein advantageously improve the accuracy and safety of performing solid organ tissue transection, and obviate the need for blind dissection.

SUMMARY

Improved devices, systems, and methods for image guided laparoscopic surgery are set forth herein. Devices, systems, and methods for image guided laparoscopic surgery presented herein can improve the accuracy and safety of performing solid organ tissue transection, resection, and/or removal of tissue from a solid organ, as current blind dissection techniques are obviated. Notably, vital structures (e.g., vascular structures) in the solid organ are identified in advance of dissecting the organ so that the organ transection line or plane (e.g., its location, placement, orientation, etc.) can be intelligently determined. Navigation of medical devices, such as surgical tools, to and/or around the vital structures is improved, as real-time visualization techniques are used during and throughout the surgical procedure.

In one aspect, devices for image guided laparoscopic surgery are disclosed. Such devices can comprise a shaft, a surgical component, a handle, and one or more sensors. The shaft comprises a proximal end and a terminal end that opposes the proximal end. The surgical component is disposed at the terminal end of the shaft, and the handle extends from the proximal end of the shaft. The handle comprises one or more actuating components configured to actuate the surgical component. The one or more sensors are disposed on or over the handle, and are configured to detect and/or track movement of the handle and/or actuation of one or more of the actuating components.

In a further aspect, methods of performing image guided laparoscopic surgery are disclosed. An exemplary method comprises providing, a medical device and providing an imaging platform. The medical device comprises a shaft with a proximal end and a terminal end, a surgical component disposed at the terminal end of the shaft, a handle extending from the proximal end of the shaft, and one or more sensors disposed on or over portions of the handle. The method further comprises receiving real-time data from the one or more sensors and constructing a virtual reality model of the medical device using the real-time data. The method further comprises receiving a real-time ultrasound image of a solid organ for determining a plane of tissue transection, and combining the virtual reality model with the real-time ultrasound image of the solid organ to produce a composite image of the virtual reality model and the solid organ for navigating the medical device towards the plane of tissue transection. The method further comprises dividing or cutting the solid organ along the plane of tissue transection using the medical device.

In yet a further aspect, systems for image guided surgery are provided herein. In one embodiment, a system comprises a medical device, an ultrasound wand, an imaging platform, a first sensor or plurality of sensors, and a second sensor or plurality of sensors. In some cases, the medical device comprises a shaft having a proximal end and a terminal end, a surgical component (such as a pair of opposing jaw members) disposed at the terminal end of the shaft, and a handle extending from the proximal end of the shaft. The handle comprises one or more actuating components configured to actuate the surgical component disposed at the terminal end of the shaft. The first sensor or plurality of sensors is disposed on or over portions of the handle, and the second sensor or plurality of sensors is disposed on or over portions of the ultrasound wand. The imaging platform is configured to generate a series of real-time images for navigating the medical device towards a solid organ using data obtained from the first sensor or plurality of sensors and the second sensor or plurality of sensors.

It is to be understood that the subject matter described herein can be implemented in software in combination with hardware and/or firmware. For example, the subject matter described herein can be implemented in software executed by a processor. In an exemplary implementation, the subject matter described herein can be implemented using a non-transitory computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits (ASICs). In addition, a computer readable medium that implements the subject matter described herein may be located on a single device or computing platform or may be distributed across multiple devices or computing platforms. As used herein, the term "computing platform" refers to a physical computing platform including one or more processors and memory.

Thus, in another aspect, a non-transitory computer readable medium for image guided laparoscopic surgery is described herein. In some cases, the computer readable medium has stored thereon executable instructions that, when executed by the processor of a computer, control the computer to perform steps for generating an image for image guided laparoscopic surgery, as described further herein.

These and other embodiments are described in more detail in the detailed description which follows.

BRIEF DESCRIPTION OF THE DRAWINGS

The accompanying drawing figures or FIGS. incorporated in and forming a part of this specification illustrate several aspects of the disclosure, and together with the description serve to explain the principles of the disclosure.

DETAILED DESCRIPTION

Devices, systems, and methods of performing image guided laparoscopic surgery are described herein, As described further herein, the devices, systems, and methods of the present disclosure improve the ability to navigate intra-parenchymal vascular and other vital structures intra-operatively for safe intra-parenchymal dissection, division, and/or parenchymal removal or resection. Devices, systems, and methods herein are more precise and safe, as surgical components can be accurately navigated, intra-operatively, to or around vital structures while avoiding inadvertent injury thereto.

It will be understood that, although the terms "first", "second", etc. may be used herein to describe various elements, those elements should not be limited by these terms. These terms are only used to distinguish one element from another. For example, a first element could be termed a second element, and, similarly, a second element could be termed a first element, without departing from the subject matter disclosed and envisioned herein. As used herein, the term "and/or" includes any and all combinations of one or more of the associated listed items.

All ranges disclosed herein are understood as encompassing any and all subranges subsumed therein. For example, a stated range of "1.0 to 10.0" is understood as including any and all subranges beginning with a minimum value of 1.0 or more and ending with a maximum value of 10.0 or less, e.g., 1.0 to 5.3, or 4.7 to 10.0, or 3.6 to 7.9.

In addition, all ranges disclosed herein are understood as including the end points of the range, unless expressly stated otherwise. For example, ranges of "between 5 and 10", "about 5 to 10", "5 to 10", or "5-10" are understood as including the recited end points 5 and 10.

Additionally, in any disclosed embodiment, the terms "substantially," "approximately," and "about" may be substituted with "within [a percentage] of" what is specified, where the percentage includes 0.1, 0.5, 1, 5, and 10 percent.

The terms "a" and "an" are defined as "one or more" unless this disclosure explicitly requires otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a composition or other object that "comprises," "has," "includes" or "contains" one or more elements possesses those one or more elements, but is not limited to possessing only those elements. Likewise, a method that "comprises," "has," "includes" or "contains" one or more steps possesses those one or more steps, but is not limited to possessing only those one or more steps.

Moreover, any embodiment of any of the devices, systems, and methods described herein can consist of, or consist essentially of—rather than comprise/include/contain/have—any of the described steps, elements, and/or features. Thus, in any of the claims, the term "consisting of" or "consisting essentially of" can be substituted for any of the open-ended linking verbs recited above, in order to change the scope of a given claim from what it would otherwise be using the open-ended linking verb.

The devices, systems, and methods for image guided laparoscopic surgery described herein are not limited to the specific embodiments presented in the detailed description, examples, and/or figures. It should be recognized that the exemplary embodiments herein are merely illustrative of the principles of the present invention. Numerous modifications and adaptations will be readily apparent to those of skill in the art without departing from the scope of the invention.

I. Devices for Image Guided Laparoscopic Surgery

In one aspect, devices for image guided laparoscopic surgery are provided. Such devices improve the ease and ability to target structures and navigate solid organ tissue intra-operatively, in part, by modeling the surgeon's actions while using the device and/or the device's spatial location relative to the patient and/or the patient's organ. In some aspects, the spatial location of the device is determined using real-time data received from an ultrasound device (e.g., ultrasound wand) which serves as a point of reference before and/or during the laparoscopic surgery.

Briefly, devices for image guided laparoscopic surgery described herein, in some embodiments, comprise a shaft; a surgical component disposed at a terminal end of the shaft; a handle extending from a proximal end of the shaft; and one or more sensors disposed on or over portions of the shaft, the surgical component, and/or the handle. In some cases, the sensors may only be disposed on or over the handle. In other instances, the sensors may only be disposed on or over the shaft. In still other embodiments, the sensors may only be disposed on or over the surgical component. A sensor or plurality of sensors may also be disposed over a combination of the shaft, handle, and surgical component, while at least one of the shaft, handle, and surgical component is devoid of sensors. Further, wherever placed, the one or more sensors generally obtain data used to virtually model the device and/or its relative movements (e.g., the relative spatial movements thereof and/or movements of components disposed thereon) for improved navigation to and/or through the solid organ tissue before, during, and after surgery.

Turning now to specific components of devices for image guided laparoscopic surgery, and in some embodiments, the shafts of devices set forth herein comprise a proximal end and a terminal end that opposes the proximal end. The proximal end of the shaft is disposed more proximate to a handle, and the terminal end of the shaft is disposed more distal from the handle but more proximate to a patient and/or a patient's solid organ. A surgical component (e.g., a cutting component, a shearing component, a sealing and/or dividing component, etc.) is disposed at the terminal end of the shaft. The proximal end of the shaft can be permanently affixed (i.e., coupled, connected, attached, etc.) to the handle or temporarily or reversibly affixed to the handle.

In some embodiments, multiple shafts and thus, multiple surgical components, are interchangeable with respect to a single handle. In other embodiments, each handle is permanently fitted with a shaft and surgical component affixed to the end of the shaft. The shaft can be substantially tubular and/or hollow, so that the surgical component disposed at the terminal end thereof can be controlled via mechanical and/or electrical controls disposed inside and/or through the shaft, and extending between the handle and the surgical component. Such mechanical and or electrical controls can comprise mechanical linkages or actuators, electrical actuators/drivers, electrical circuits, electrically conductive wires, electrical devices (e.g., resistors, transistors, switches, controllers, etc.), etc.

As persons having skill in the art will appreciate, the actuation (e.g., rotation, articulation, opening/closing, sealing, etc.) of the surgical component disposed at the terminal/distal end of a laparoscopic device can be performed by any combination of mechanical and/or electrical components not inconsistent with the instant disclosure. In some embodiments, movement of the shaft (e.g., rotation, articulation, etc.) is also controlled via electrical and/or mechanical controls extending therethrough. Movements, location, and/or position of the device, shaft, and/or surgical component can be detected and/or tracked via attaching one or more sensors to the medical device. Sensors may be attached to the handle, shaft, actuating components on the handle, and/or the surgical component.

The shaft can have a shaft length of about 20-50 centimeters (cm) or any subrange therebetween, such as, for example and without limitation, a shaft length of about 20-25 cm; about 32-38 cm; or about 40-45 cm. The shaft length may be customized for a given patient size, gender, age, body type, or selected based upon the specific type and/or location of the laparoscopic surgery. In certain embodiments, multiple shafts comprised of various lengths can be provided in a single medical kit for use with one or more handles and/or surgical components. For example, a kit may consist of a handle that is interchangeable with shafts having respective shaft lengths of 23 cm, 37 cm, and 44 cm. As persons having skill in the art will appreciate, a shaft and/or kits comprised of multiple shafts can be formed in any length that is not inconsistent with the instant disclosure.

Further, the shaft can have any diameter that is not inconsistent with the instant disclosure. For example and in some embodiments, the shaft of devices described herein can comprise a shaft diameter of about 2-10 millimeters (mm) or any subrange therebetween, such as, for example and without limitation, a shaft diameter of about 2-8 mm; about 2-6 mm; or about 3-5 mm. Devices described herein can comprise a shaft that averages about 5 mm in diameter. However, as persons having skill in the art will appreciate, devices having a shaft diameter of less than 5 mm or more than 5 mm (e.g., up to about 10 mm), can also be provided and used for laparoscopic surgery.

Devices set forth herein further comprise a surgical component disposed at the terminal end of the shaft. The term "surgical component" refers to the component disposed at the terminal or distal end of a respective shaft that contacts a patient's tissue (e.g., parenchyma) before and/or during surgery. A surgical component can comprise any type of tool, instrument and/or device that is used during a laparoscopic procedure consistent with the instant disclosure, including, but not limited to cutting components, sealing and/or dividing components (e.g., a bipolar vessel sealing component), laparoscopic stapling components, suturing components, scissors/shears, graspers, dissectors, hooks, knifes, spatulas, laparoscopic forceps, etc. In certain embodiments, surgical components described herein comprise a pair of opposing jaw members. The jaw members may be configured to open and close to facilitate grasping, cutting, shearing, and/or vessel sealing and division. The jaws may also be configured to support and expel a staple for laparoscopic tissue stapling. Surgical components may also be devoid of jaw members, where desired. Placement of sensors on or over the medical device can be used to track the actuation, location, movement, and/or position of the surgical components during surgery.

Additionally, the surgical component provided or disposed at the terminal end of the shaft can be mechanically and/or electrically coupled and/or controlled by the handle. For example, the surgical component can be actuated and/or controlled via actuating components disposed on or over the handle, for example, by manipulating (e.g., moving, grasping, rotating, squeezing, releasing, turning, etc.) actuating components that are disposed on or over the handle. The mechanical and/or electrical controls can be communicated via mechanical and/or electrical linkages extending between portions of the handle and surgical component and housed within the shaft. In an exemplary embodiment, a surgical component comprising a pair of opposing jaw members can be instructed or controlled to open, close, and/or electrically activate for vessel sealing and division. A surgeon can control the surgical component via manipulating portions of the handle. The actions or movements used to manipulate the handle, or portions thereof, can be tracked via tracking the location, movement, and/or position of sensors attached thereto.

Moreover, the handle of a respective device can comprise a gripping portion or region whereby the user grips the device and one or more actuating components disposed thereon. A user (e.g., surgeon) may manipulate the one or more actuating components during surgery, and cause the shaft and/or the surgical component attached thereto to actuate in response to movement of the actuating component. For example, moving and/or manipulating one or more actuating components on the handle can cause the shaft or surgical component to rotate, articulate, move, pivot, slide, cut through tissue, open/close, seal tissue (e.g., via application of electrical current), etc. Such movement can be detected or tracked using sensors, such as field actuated sensors.

The term "actuating component" refers to a manipulable component disposed on or over the handle which induces an action or movement of the shaft, surgical component, or portions thereof, to which it is electrically, mechanically, or otherwise connected. Exemplary actuating components include a trigger, a button, a knob, a dial, a lever, etc., which induce the shaft, surgical component, and/or portions thereof to move, rotate, articulate, open, close, or electrically activate for tissue sealing or division. Sensors can be placed on or over the actuating components for tracking the actuation thereof during surgery, so that an accurate virtual model may be constructed for real-time visualization of the trajectory and device movement (e.g., opening/closing of the jaw members) during tissue transection.

As noted above and in farther embodiments, devices for image guided laparoscopic surgery as described herein can further comprise one or more sensors disposed on or over portions of the handle, shaft, and/or surgical component for detecting or tracking movement of the handle and/or actuation of one or more of the actuating components. The sensors can be field activated, that is, they can react to an electromagnetic field, such as a field generated by a field generating device. The field generating device, in some embodiments, is placed proximate to the patient's body during surgery. In certain embodiments, the field generator comprises a rigid or formable pad that is disposed over/under the patient's body on a front or back side that opposes the back or front side that faces the surgeon. In certain embodiments, the field generator device comprises a rigid or formable pad that is disposed between the patient's body and the operating table, and is optionally in contact with both.

The one or more sensors are configured to track or detect movement of the entire device, or components thereof (e.g., movement of the shaft and/or handle), and/or actuation of one or more of the actuating components. That is, sensors may be disposed on, over or proximate to actuating components so that actions of moving the actuating components are detected and/or tracked. Such actions may include depressing a button, squeezing a trigger, rotating a dial, etc.

In some embodiments, the one or more sensors are activated by the field generating device and the location, position, and/or movement thereof is tracked via a position sensing system. The position sensing devices and/or systems described herein are configured to detect movement and/or the position of a medical device, or components thereof, via tracking the movement and/or position of the sensors attached thereto.

In exemplary embodiments, the sensors described herein include, for example, magnetic coils that are tracked via a position sensing unit such as Ascension Flock of Birds, Nest of Birds, driveBAY, medSAFE, trakSTAR, miniBIRD, MotionSTAR, pciBIRD, or Calypso 4D Localization System. In other embodiments, the sensors may include an Aurora® Electromagnetic Measurement System that uses sensor coils for tracking the movement and position of the medical device, or portions thereof. In other embodiments, sensors are tracked via optical 3D tracking systems such as the NDI Polaris Spectra, Vicra, Certus, PhaseSpace IMPULSE, Vicon MX, InterSense IS-900, NaturalPoint OptiTrack, Polhemus FastTrak, IsoTrak, or Claron MicronTracker. In further embodiments, sensors are tracked via a HiBall tracking system, a GPS device or signal emitting device that would allow for tracking of the position and, optionally, orientation of the tracking unit.

A point of reference, such as an ultrasound wand in some embodiments, may also be tracked using sensors in order to determine the movement of the medical device with respect to the wand, and thus, the solid organ. Sensors may optionally include and/or be coupled to one or more accelerometers used to estimate the movement, position, and location of the medical device and/or portions thereof.

Notably, the position, location, and/or movement of the sensors is tracked so that rotation and/or linear translation of the handle can be tracked or detected. Movements and/or positions that indicate actuation of one or more of the actuating components are also tracked or detected so that a resultant virtual reality model accurately models actuation of the surgical component (e.g., opening of the jaw members, closing of the jaw members, etc.). Sensors can also be disposed over one or more portions of the shaft or surgical component so that movements and/or positions that indicate rotation and articulation of the shaft and/or movement of the components are also tracked or detected. Tracking the position, location, and/or movement of the medical devices, or portions thereof, relative to the solid organ greatly improves the ability to navigate the device to or around vital structures during laparoscopic procedures, such as during tissue resection or removal.

Persons skilled in the art will appreciate that the device, and/or portions thereof as described hereinabove, may be separated, combined, and/or integrated into one or more components, as desired, for accomplishing accurate targeting, navigating, sealing, dividing, cutting, and/or stapling procedures during image guided laparoscopic surgery described herein.

Additionally, it is to be understood that, as used herein the term "solid organ" refers to an internal organ having a firm tissue consistency that is neither hollow nor liquid, such as the kidney, liver, spleen, or pancreas.

II. Systems for Image Guided Laparoscopic Surgery

In another aspect, systems for image guided surgery are described herein. Such a system can comprise a medical device, an ultrasound wand, a first sensor or plurality of sensors disposed over the handle of the medical device, and a second sensor or plurality of sensors disposed over portions of the ultrasound wand. The system can further comprise an imaging platform configured to generate a series of real-time images for navigating the medical device towards a solid organ using data obtained from the first sensor or plurality of sensors and the second sensor or plurality of sensors. The series of images are a composite image constructed from location/position data obtained from sensors disposed on the medical device, location/position data obtained from sensors disposed on the ultrasound device, and volumetric data obtained from the ultrasound device.

Briefly, the medical device can comprise any device described hereinabove in Section I. For example, the a medical device can comprise a shaft, a surgical component comprising a pair of opposing jaw members disposed at the terminal end of the shaft, and a handle extending from the proximal end of the shaft. The handle can include at least one actuating component configured to actuate the pair of opposing jaw members.

Notably, movements that activate an actuating component can be detected via tracking the movement, position and/or location of one more sensors disposed on, over, or proximate the actuating component, as described above. For example and in one exemplary embodiment, an actuating component is a trigger, and a sensor can be disposed on the trigger. When the trigger is pulled, the jaw members automatically close, causing a staple to be ejected and expelled into tissue for closing the tissue. The movement of pulling the trigger is detected and tracked via the sensor, and used to virtually model the medical device relative to a point of reference on the solid organ. The motion of pulling the trigger is used to generate a model of intraoperative stapling via the medical device.

Likewise, models al articulating the shaft/surgical component relative to the handle, rotating the shaft/surgical component relative to the handle, and other movements such as the opening/closing of the jaws of the surgical component can also be constructed, at least in part, by modeling the movement, location, or position of the actuating components on the handle of the medical device via sensors.

Additionally, in some cases, the position of the medical device relative to the solid organ can be modeled using sensors disposed on or over a point of reference. In an exemplary embodiment, the point of reference includes an ultrasound device or wand. For example, a first sensor or plurality of sensors can be disposed on/over portions of the handle of a medical device and a second sensor or plurality of sensors disposed on/over portions of the ultrasound wand. Thus, the relative spatial position of the medical device with respect to the ultrasound wand can be detected. The ultrasound wand can also be in contact with the solid organ, and used to visualize real-time 3D images of the organ using volumetric data obtained during a 3D ultrasound. Thus, vascular pedicles and vital structures can be visualized, targeted, and/or navigated when the real-time virtual reality model of the medical device is overlaid or combined with the real-time 3D ultrasound image.

In some embodiments, the ultrasound wand provided in a system described herein comprises a 3D ultrasound transducer configured to capture real-time (or near real-time) volumetric data of a solid organ. In some embodiments, a volumetric image is captured and vital structures can be identified and/or marked prior to dissection so that the virtually modeled medical device can be navigated to or around such structures during tumor resection or tissue removal. The position and orientation of the medical device relative to the ultrasound wand and organ are continuously updated as the physician moves the device. The position and ultrasound data can be combined and visualized on a 2D interface (e.g., display screen) or a 3D interface (e.g., virtual reality headset), as described in U.S. Pat. No. 8,690,776, which is incorporated herein by reference in its entirety.

Systems described herein further comprise an imaging platform configured to generate a series of real-time images for navigating the medical device towards a solid organ. The real-time images are composite images constructed from data obtained from the first sensor or plurality of sensors, the second sensor or plurality of sensors, and 3D ultrasound images. In some embodiments, the data obtained from the first and second sensors or pluralities of sensors includes position or location data that tracks the relative spatial position of the medical device relative to the ultrasound wand and solid organ. The data obtained from the sensors can be combined, overlaid, merged, fused, or otherwise presented simultaneously with volumetric data obtained from the 3D ultrasound wand. The different types of data are displayed simultaneously so that a surgeon has improved visualization of the surgical trajectory and vital structures within a solid organ.

In some embodiments, position sensing units are used to track the sensors disposed on the medical device and the ultrasound wand. The position data is sent to the imaging platform, which processes or combines the data with the volumetric data obtained from the 3D ultrasound transducer and provided on a display. The imaging platform displays the combined images (i.e., virtual reality model and volumetric image) for guiding a procedure and improving care.

Different data (i.e., position data, volumetric data) from two or more devices (i.e., medical device and ultrasound wand) may be combined and displayed based on their relative placements or configurations. For example, an ultrasound image may be displayed with respect to an endoscopic linear stapling device, a bipolar vessel sealing device, or a device comprising harmonic coagulating shears on a display so that estimates of the relative placements or configurations of the ultrasound wand and medical device are provided. An example of obtaining and combining data and graphics from different medical devices is available, for example, in U.S. Pat. No. 8,690,776.

The imaging platform described herein can be a special purpose computer that is suitable for use in performing the functions described herein, namely combining various forms of imaging data received from different devices and constructing improved real-time images of infra-operative devices and structures during laparoscopic surgery.

In some cases, the imaging platform includes at least one processor and memory. The processor may be a physical hardware processor including a single core or multiple cores. The processor may also be a virtual processor that runs on a hypervisor layer that control access to underlying processor hardware. The memory may be volatile or non-volatile memory that stores instructions executed by the processor. As with the processor, the memory may be a physical memory chip or virtualized memory that is mapped to one or more physical memory chips by a hypervisor layer.

The memory is configured to store and/or access an image generating module and data. As used herein, the term "module" refers to software in combination with hardware and/or firmware for implementing features described herein. The image generating module has access to different types of real-time data received from multiple medical devices, including an ultrasound wand. The image generating module can combine the spatial data received from one or more sensors disposed on the multiple medical devices with ultrasound data, generate a composite image, and output the composite image for display on a display device. For example and in some embodiments, the image generating model is configured to receive sensor data and ultrasound data. The sensor data is used to construct an image via a virtual reality model existing in the memory of the imaging platform, and the ultrasound data is used to construct an image from a solid organ model existing in the memory of the imaging platform. The resultant images are constructed, combined and displayed as a composite image, or a series of images that are continuously updated using the real-time data.

Persons skilled in the art will appreciate that the system and/or portions thereof as described hereinabove, may be separated, combined, and/or integrated into one or more components, as desired, for accomplishing accurate mapping, imaging, dissecting, transecting, dividing, removing, targeting and/or resecting procedures during image guided laparoscopic surgery described herein.

III. Methods of Performing Image Guided Laparoscopic Surgery

In a further aspect, methods of performing image guided laparoscopic surgery are described herein. Such a method can comprise providing a medical device and providing an imaging platform. Briefly, the medical device can comprise any device described hereinabove in Section I. The imaging platform can be a special purpose computer or computing device as described hereinabove in Section II.

A method of performing image guided laparoscopic surgery can further comprise receiving, at the imaging platform, real-time data from the one or more sensors disposed on or over portions of the handle and constructing a virtual reality model of the medical device using the real-time data. The real-time data received from the one or more sensors can comprise position, location, and/or orientation data regarding the device's 3D spatial location relative to a point of reference. In some embodiments, the point of reference includes an ultrasound device or wand.

Further, the method can include receiving, at the imaging platform, a real-time ultrasound image of a solid organ for determining a plane of tissue transection. The real-time ultrasound image of the solid organ can contain volumetric data, and comprise a 3D ultrasound image. The plane of tissue transection can be determined using visual imaging data intra-operatively, so that vital structures can be avoided upon transection of the solid organ.

Methods of preforming image guided laparoscopic surgery, in some embodiments, further include combining, at the imaging platform, the virtual reality model with the real-time ultrasound image of the solid organ to produce a composite image of the virtual reality model and the solid organ for navigating the medical device towards the plane of tissue transection.

Additionally, the method can further comprise dividing the solid organ along the plane of tissue transection using the medical device. Moreover, when the organ is being divided, vital structures can be avoided, and after the organ is divided, the surgical component can be more accurately navigated to an area of interest or removed from the patient.

Persons skilled in the art will appreciate that the methods as described hereinabove are exemplary, as some steps may be combined, integrated, separated, and/or additional steps may be performed so long as the steps are not inconsistent with the objectives of the present disclosure.

IV. Computer Readable Medium for Image Guided Laparoscopic Surgery

In yet a further aspect, a non-transitory computer readable medium for image guided laparoscopic surgery is described. The computer readable medium has stored thereon executable instructions that when executed by the processor of a computer control the computer to perform steps for generating an image for image guided laparoscopic surgery.

In some embodiments, generating an image for image guided laparoscopic surgery includes receiving, at the processor of an imaging platform, real-time data from one or more position sensors disposed on or over portions of a handle of a medical device and constructing a virtual reality model of the medical device using the real-time data.

In some cases, generating an image further comprises receiving, at the processor of an imaging platform, a real-time ultrasound image of a solid organ for determining a plane of tissue transection. The real-time image can be 3D, or contain volumetric data.

Moreover, generating an image can comprise combining the virtual reality model with the real-time ultrasound image of the solid organ to produce a composite image of the virtual reality model and the solid organ. The image is used for improved visualization and navigation of a medical device towards the plane of tissue transection during a laparoscopic procedure.

Persons skilled in the art will appreciate that the subject matter described hereinabove are exemplary, as some steps may be combined, integrated, separated, and or additional steps may be performed so long the steps are not inconsistent with the objectives of the present disclosure.

Some embodiments described herein are further illustrated in the following non-limiting examples, and reference will be made in detail to possible aspects or embodiments of the subject matter herein, one or more examples of which are shown in the figures (i.e., "FIGS."). Each example is provided to explain the subject matter and not as a limitation. In fact, features illustrated or described as part of one embodiment can be used in another embodiment to yield a further embodiment. It is intended that the subject matter disclosed and envisioned herein covers such modifications and variations.

EXAMPLE 1

Devices for Image Guided Laparoscopic Surgery

Figure 1:
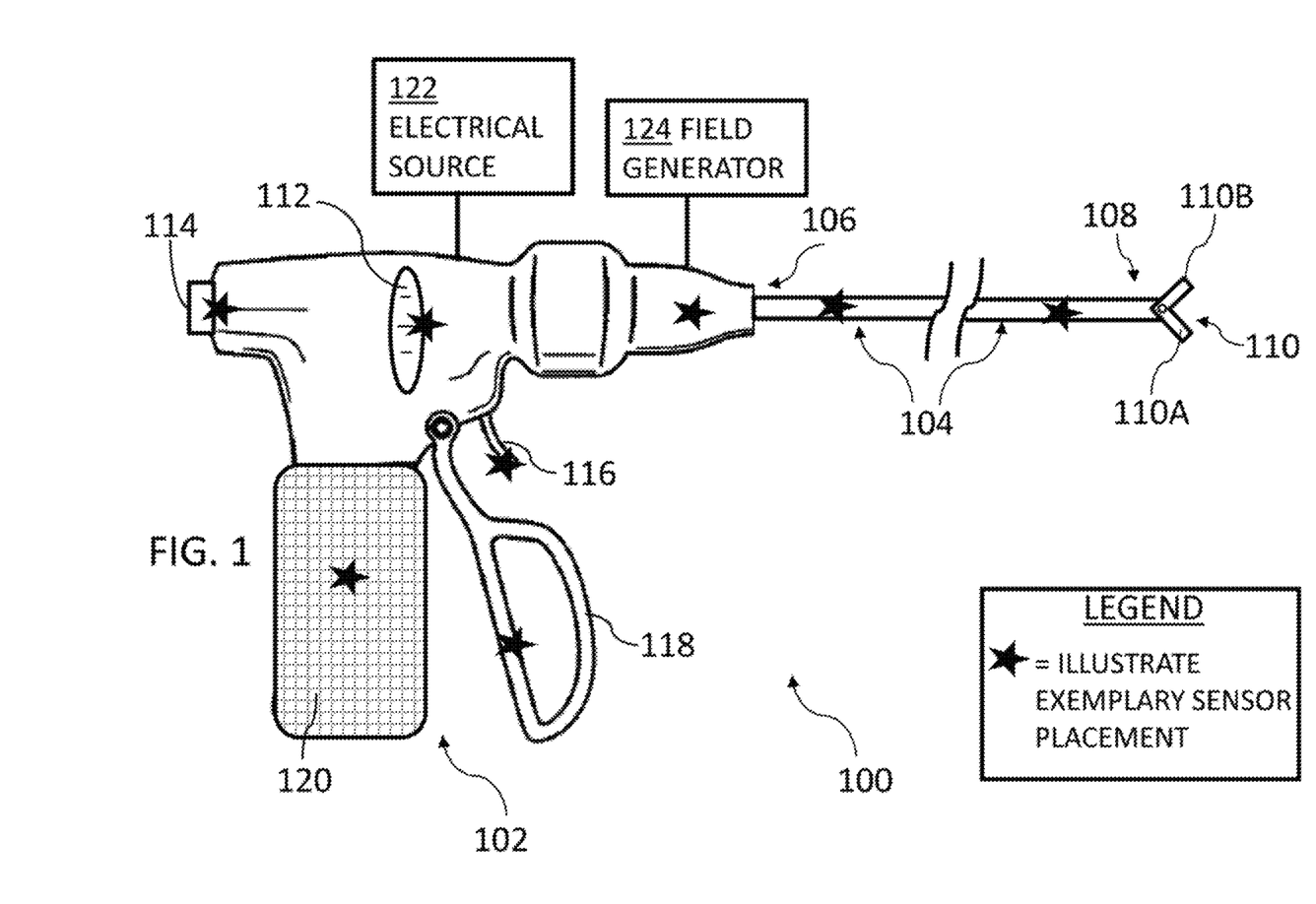
FIG. 1 is a side view of a device for image guided laparoscopic surgery according to one embodiment described herein.

FIG. 1 is a side view of a device, generally designated 100 for image guided laparoscopy according to sonic embodiments described herein. Device 100 includes a handle 102 and a shaft 104 that extends from the handle. Shaft 104 can comprise a proximal end 106 that is adjacent to handle 102, and a distal or terminal end 108 that is opposite the handle. A surgical component 110 is disposed at distal end 108. For illustration purposes only, a single medical device 102 is shown in FIG. 1. However, it will be appreciated that the features, functionality, and/or concepts described herein are applicable to many different types of medical devices, including, but not limited to endoscopic linear stapling devices, bipolar vessel sealing devices, or devices comprising harmonic coagulating shears.

Handle 102 comprises one or more actuating components (i.e., 112, 114, 116, and 118) configured to actuate a pair of opposing jaw members 110A, 110B disposed at terminal end 108 of shaft 104. While many different types of actuating components are illustrated in FIG. 1, any of such components are optional. For example and in some embodiments, device 100 can comprise a first actuating component 112, a second actuating component 114, a third actuating component 116, and/or a fourth actuating component 118. More or less than four actuating components may be provided, where desired. The location of each actuating component may also be different than that shown, and even customized, where desired. It will be appreciated that different types of actuating components may also be provided on or over device 102, other than those specifically shown.

In some embodiments, first actuating component 112 comprises a rotatable knob or dial that extends through a transverse, sectional portion of handle 102. Portions of the dial are provided on either side of handle 102 for accommodating both right- and left-handed users. First actuating component 112 can be activated via manual rotation, for example, by urging the dial substantially orthogonal (up/down) relative to the shaft's longitudinal extension. The dial may actuate movement of the shaft 104 or surgical component 110. For example, moving the dial may result in rotation, articulation, or other movement of shaft 104 and/or surgical device 110 relative to handle 102.

Second actuating component 114 can comprise a pressure sensitive control, such as a push-button control. The location of second actuating component 114 is also accessible to both right- and left-handed users. Second actuating component 114 can be activated via application of pressure, for example, by pressing the control substantially towards the proximal end 106 of shaft 104 (e.g., substantially parallel to the shaft's extension). The push-button control may actuate the shaft 104 and/or surgical device 110 via rotation, articulation, or other movement thereof relative to handle 102. Push button control may also actuate jaw members 110A, 110B of the surgical component for grasping or manipulating tissue in the patient's body.

Third actuating component 116 may also comprise a pressure actuated or pressure sensitive control, such as a trigger. Pulling the trigger control (i.e., 116) towards a gripping portion 120 of handle 102 (i.e., towards the surgeon/user) may actuate jaw members 110A, 110B of surgical component 110 to close and seal a vessel in the patient's body. For example, squeezing the trigger may cause the jaw members 110A, 110B to close (i.e., move towards each other) and squeeze against a vessel or tissue and apply an electrical current thereto for electrically sealing the vessel or tissue.

In further embodiments, squeezing the trigger (i.e., 116) may actuate jaw members 110A, 110B of surgical component 110 to eject, expel, and enclose portions of a vessel/vascular structure within a disposable staple supported thereon. The closing action or opposing jaw members 110A, 110B may eject or expel the disposable staple into the organ for adequately sealing a vessel as the vessel is clamped between opposing portions of the staple. Trigger control (i.e., 116) may also actuate jaw members 110A, 110B to open and close for dividing or cutting tissue, where desired. Jaw members 110A, 110B may be configured to cut, shear, divide, and/or seal tissue laparoscopically.

Still referring to FIG. 1 and in some embodiments, fourth actuating component 118 can comprise a pressure sensitive control, whereby squeezing the component against gripping portion 120 of handle 102 actuates the surgical device 110 to cut, divide tissue, seal tissue, etc. Squeezing fourth actuating component 118 against gripping portion 120 may also cause electrical current to pass from an electrical power source 122 to surgical component 110 for sealing the tissue via application of electrical current thereto.

As FIG. 1 further illustrates, the solid star (★) shapes indicate exemplary placement locations of one or more sensors on or over device 100. Only one sensor may be disposed on/over device 100, or multiple sensors may be disposed on/over device 100. In some embodiments, sensors are disposed on/over portions of handle 102 for tracking the location, position, movement, and/or orientation of the handle 102. Other portions of device 100 may optionally be devoid of sensors, for example, surgical component 110 or shaft 104 may optionally be devoid of sensors. In other embodiments, shaft 104 and/or surgical components 110 include sensors for tracking the location, position, movement, and/or orientation thereof relative to a point of reference.

In further embodiments, sensors are disposed on/over the one or more actuating components (i.e., 112, 114, 116, or 118) so that the result of activating the actuating component (i.e., the articulation, rotation, closing/opening of jaws, etc.) can be modeled and/or tracked. The sensors can be activated by a field generator 124, which generates an electromagnetic field. Each sensor may include, for example, magnetic coils that are tracked via a position sensing unit (not shown).

It is understood that the architecture illustrated in FIG. 1 is exemplary and simplified in that device 100 may include additional or alternative components without departing from the scope of the subject matter described herein. It will further be appreciated that FIG. 1 is for illustrative purposes and that various components, their locations, and/or their functions described above in relation to FIG. 1 may be changed, altered, added, and/or removed without departing from the subject matter described herein.

EXAMPLE 2

Systems for Image Guided Laparoscopic Surgery

Figure 2:
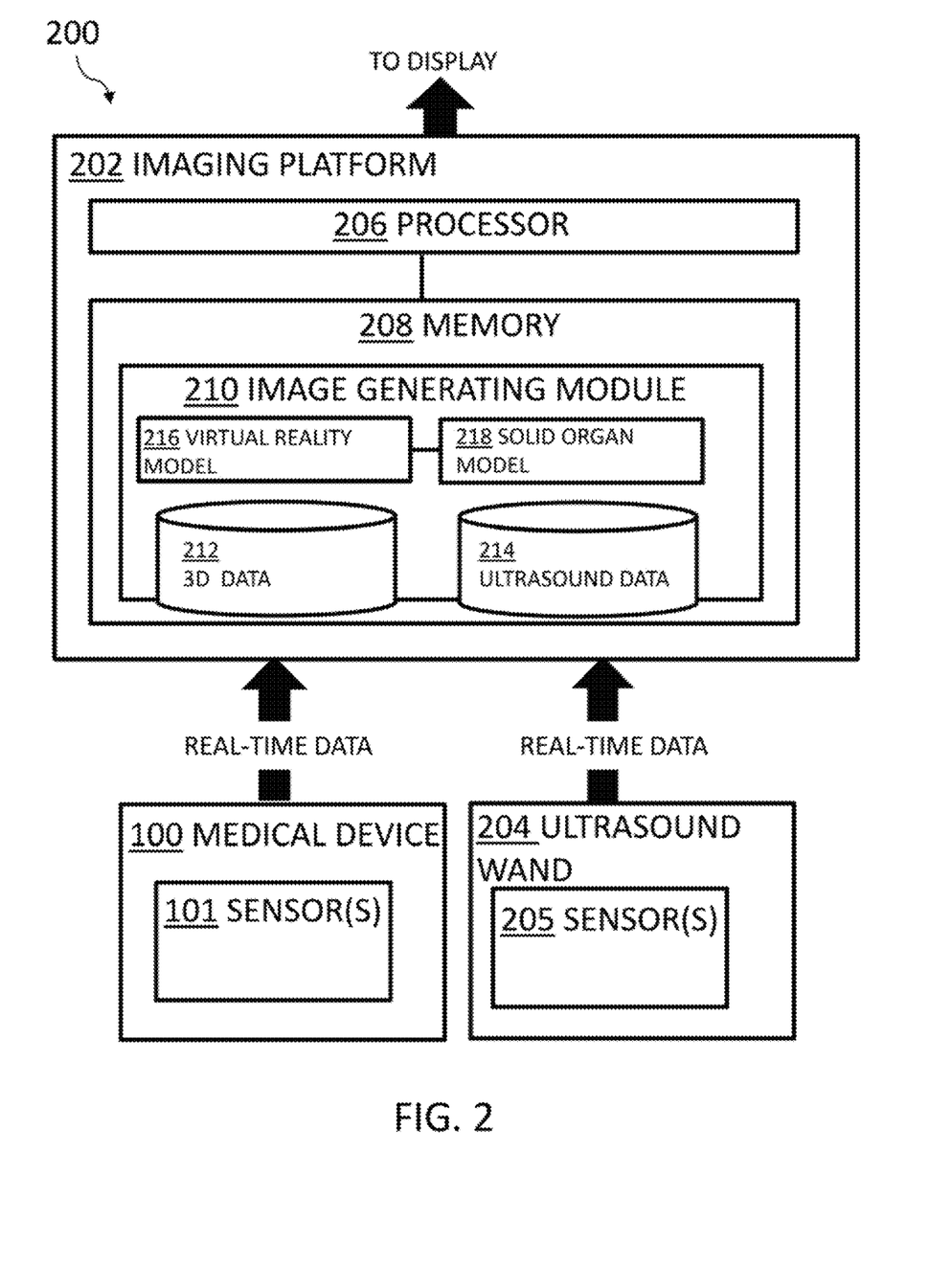
FIG. 2 is a schematic block diagram of a system for image guided laparoscopic surgery according to one embodiment described herein.

FIG. 2 is a block diagram illustrating exemplary components of a system, generally designated 200, that includes a special purpose computer for use in performing the functions described herein, namely constructing real-time, three-dimensional images from data obtained intra-operatively during a laparoscopic procedure. The data may be obtained as a surgeon actuates at least one component disposed on/over the handle of a medical device, which automatically generates a movement of a surgical component opposite the handle. The data obtained from the handle is used to virtually model movement at the surgical component.

In FIG. 2, system 200 comprises an imaging platform 202, a medical device 100 (see FIG. 1), and an ultrasound wand 204. A first plurality of sensors 101 is disposed over medical device 100 and a second plurality of sensors 205 is disposed over ultrasound wand 204. The sensors are used to track the spatial location and movement of the medical device relative to the ultrasound wand in a 3D space. The real-time time location/position data obtained via monitoring and/or tracking sensors 101, 205 is sent to imaging platform 102 and used to generate a virtual reality model.

Ultrasound wand 204 is also configured to send real-time 3D ultrasound data (e.g., volumetric data) of the sold organ to imaging platform 202. imaging platform 202 receives and/or accesses sensor data 212 and ultrasound data 214 from multiple medical devices medical device 100 and ultrasound wand 204). Imaging platform 202 uses sensor data 212 to construct a 3D virtual reality model 216 of medical device 100. Imaging platform 202 receives and/or accesses ultrasound data 214 from ultrasound wand 204 and generates a 3D solid organ model 218. The virtual reality model 216 is overlaid, fused, or combined with the solid organ model 218 for improved advanced imaging and visualization of a solid organ and a medical device navigating to/within the solid organ intra-operatively.

Imaging platform 202 is a special purpose computer that improves the technological field of image guided laparoscopic surgery, as visualization of vital structures and medical devices is improved, and such structures can be avoided during solid organ parenchymal transection. Further, medical devices can be more accurately and precisely navigated to or around vital structures during tumor resection and/or tissue removal.

Imaging platform 202 comprises at least one processor 206 and at least one memory 208. Processor 206 may be a physical hardware processor including a single core or multiple cores. Processor 206 may also be a virtual processor that runs on a hypervisor layer that control access to underlying processor hardware.

Memory 208 may be volatile or non-volatile memory that stores instructions executed by processor 206. As with processor 206, memory 208 may be a physical memory chip or virtualized memory that is mapped to one or more physical memory chips by a hypervisor layer.

In the illustrated example, memory 208 stores an image generating module 210 which accesses sensor data 212, ultrasound data 214, and generates an image via combining the sensor data and ultrasound data. Image venerating module 210 is executed via processor 206, and a composite image is constructed from the virtual reality model 216 and the solid organ volumetric data or model 218. The composite image is sent to a display whereby a plane of tissue transection is determined and medical device 100 is navigated towards the plane of tissue transection. Medical device 100 can then divide the organ along the plane of tissue transection and navigate the device through the solid organ for accurate, safe tumor resection or tissue removal.

It is understood that the architecture illustrated in FIG. 2 is exemplary and simplified in that system 200 and/or imaging platform 202 may include additional or alternative components without departing from the scope of the subject matter described herein. It will further be appreciated that FIG. 2 is for illustrative purposes and that various components, their locations, and/or their functions described above in relation to FIG. 2 may be changed, altered, added, and/or removed.

EXAMPLE 3

Method for Performing Image Guided Laparoscopic Surgery

Figure 3:
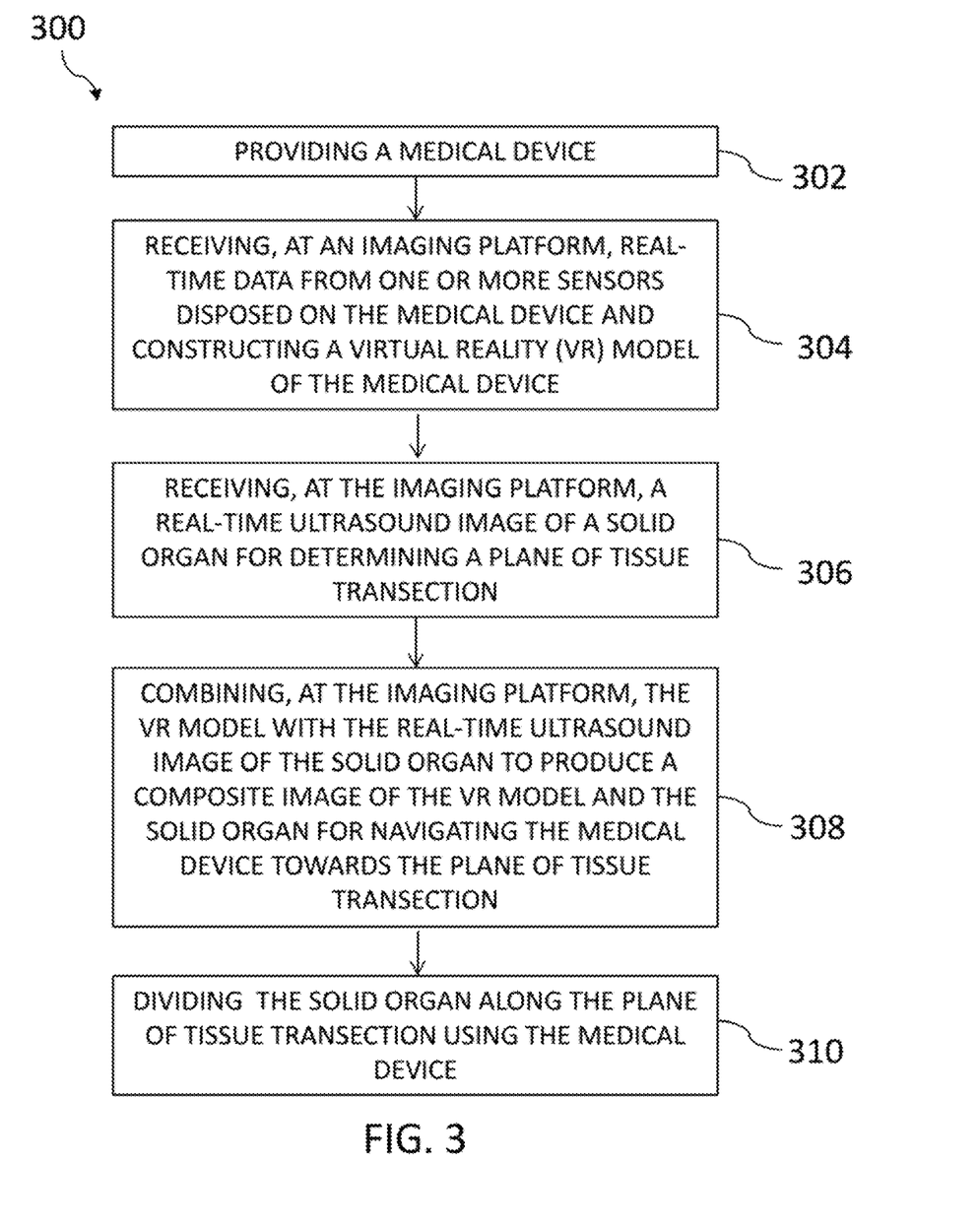
FIG. 3 is a schematic block diagram illustrating exemplary steps of a method of performing image guided laparoscopic surgery according to one embodiment described herein.

FIG. 3 illustrates an exemplary method of performing image guided laparoscopic surgery, generally designated 300. At 302, the method comprises providing a medical device. The medical device can comprises a shaft with a proximal end and a terminal end, a surgical component disposed at the terminal end of the shaft, and a handle extending from the proximal end of the shaft. One or more actuating components configured to actuate the shaft or the surgical component can be disposed on or over the handle.

An imaging platform is also provided. At 304, the method comprises receiving, at the imaging platform, real-time data from the one or more sensors disposed on or over portions of the handle and constructing a virtual reality model of the medical device using the real-time data.

In some embodiments, constructing a virtual reality model of the medical device comprises modeling the rotation, linear translation, and/or articulation of the medical device. That is, a virtual reality model can be constructed, in real time, as a surgeon rotates, linearly/axially moves, or articulates the medical device. In other embodiments, constructing the virtual reality model of the medical device comprises modeling the jaw members in real-time while opening, closing, rotating, or articulating the jaw members. In yet further embodiments, constructing the virtual reality model of the medical device comprises modeling actuation of one or more of the actuating components. That is, a virtual reality model can be constructed, in real time, as a surgeon, for example, rotates a dial, pulls or releases a trigger, or pushes a knob of a medical device. Other actuating components and actions are envisioned and contemplated herein.

At 306, the method comprises receiving, at the imaging platform, a real-time ultrasound image of a solid organ for determining a plane of tissue transection. As noted above, intraoperative ultrasound is used before and during a laparoscopic surgery, and the ultrasound wand can be embedded with directional field detectors and used as a point of reference on a series of 3D ultrasound images. The 3D ultrasound can be used to identify vascular pedicles and vital structures air determining the plane of tissue transection.

At 308, the method comprises combining, at the imaging platform, the virtual reality model with the real-time ultrasound image of the solid organ to produce a composite image of the virtual reality model and the solid organ for navigating the medical device towards the plane of tissue transection.

At 310, the method comprises dividing the solid organ along the plane of tissue transection using the medical device. In some embodiments, the capsule of the organ near the previously identified vital structures is incised with cautery or other energy device, and with real-time ultrasound a medical device with sensors and a surgical component (e.g., a stapling device) can be navigated so that the surgeon can visualize the trajectory and the stapling device to and around the vital structure for safe division. Several sequential firings of a stapler or use of an energy device may be provided to complete the tissue transection.

Various embodiments of the present invention have been described in fulfillment of the various objectives of the invention. It should be recognized that these embodiments are merely illustrative of the principles of the present invention. Numerous modifications and adaptations thereof will be readily apparent to those skilled in the art without departing from the spirit and scope of the invention.

The invention claimed is:

1. A device for image guided laparoscopic surgery, the device comprising:
 a shaft comprising a proximal end and a terminal end opposing the proximal end;
 a surgical component disposed at the terminal end of the shaft;
 a handle extending from the proximal end of the shaft;
 one or more actuating components coupled to the handle, the one or more actuating components being configured to actuate the surgical component; and
 a plurality of sensors disposed on or over the handle, wherein at least one of the plurality of sensors is configured to track or detect actuation of the one or more actuating components;
 an imaging platform in operative communication with the plurality of sensors and configured to construct a three-dimensional virtual reality model of the device using real-time data received from the plurality of sensors and based at least in part on the actuation of the one or more actuating components.

2. The device of claim 1, wherein the plurality of sensors are further configured to track or detect at least one of rotational movement and linear translation of the handle.

3. The device of claim 1, wherein the one or more actuating components comprises a trigger, a button, a knob, or a dial.

4. The device of claim 1, wherein one or more of the plurality of sensors are field activated sensors.

5. The device of claim 1, wherein one or more of the plurality of sensors are activated by a field generating device.

6. The device of claim 1, wherein the shaft has a length of about 20-50 centimeters (cm).

7. The device of claim 1, wherein the shaft has a diameter of about 2-10 millimeters (mm).

8. The device of claim 1, further comprising one or more sensors disposed on or over a portion of the shaft and/or a portion of the surgical component.

9. The device of claim 8, wherein the three-dimensional virtual reality model of the device is constructed using real-time data received from the one or more sensors disposed on or over a portion of the shaft and/or a portion of the surgical component.

10. The device of claim 1, wherein the surgical component is devoid of sensors.

11. The device of claim 1, wherein the surgical component comprises a pair of opposing jaw members for vessel sealing and division.

12. The device of claim 11, wherein the pair of opposing jaw members are powered via an electrical source for effecting the vessel sealing and division.

13. The device of claim 1, wherein the surgical component comprises a pair of opposing jaw members configured to support and expel a staple for laparoscopic tissue stapling.

14. The device of claim 1, wherein the surgical component comprises a pair of harmonic coagulating shears.

* * * * *